US00PP35022P2

(12) United States Plant Patent
Bisschop et al.

(10) Patent No.: US PP35,022 P2
(45) Date of Patent: Mar. 7, 2023

(54) ***CAREX* PLANT NAMED 'ET CRX 904'**

(50) Latin Name: ***(Carex morrowii* X *Carex oshimensis)* X *Carex trifida***
Varietal Denomination: ET CRX 904

(71) Applicant: ETERNAL PLANT BOIJL B.V., Boijl (NL)

(72) Inventors: Elisabeth Bisschop, Boijl (NL); Bart Noordhuis, Boijl (NL)

(73) Assignee: ETERNAL PLANT BOIJL B.V., Boijl (NL)

( * ) Notice: Subject to any disclaimer, the term of this patent is extended or adjusted under 35 U.S.C. 154(b) by 0 days.

(21) Appl. No.: 17/941,912

(22) Filed: Sep. 9, 2022

(51) Int. Cl.
*A01H 5/12* (2018.01)

(52) U.S. Cl.
USPC ..... Plt./384

(58) Field of Classification Search
USPC ..... Plt./384
See application file for complete search history.

*Primary Examiner* — Annette H Para
(74) *Attorney, Agent, or Firm* — C. Anne Whealy

(57) ABSTRACT

A new and distinct cultivar of *Carex* plant named 'ET CRX 904', characterized by its relatively compact and broad outwardly arching plant habit; moderately vigorous to vigorous growth habit; long linear yellow green, light yellow and white variegated leaves; and good garden performance.

3 Drawing Sheets

Figure 1:
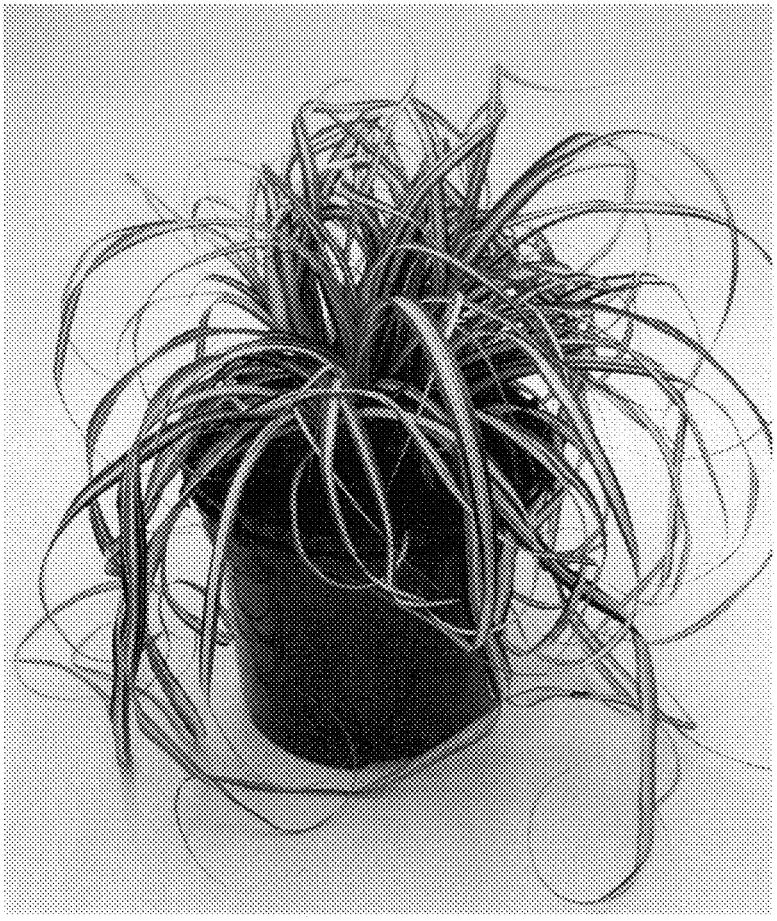

Botanical designation: (*Carex morrowii* X *Carex oshimensis*) X *Carex trifida*.
Cultivar denomination: 'ET CRX 904'.

BACKGROUND OF THE INVENTION

The present invention relates to a new and distinct *Carex* plant, botanically known as (*Carex morrowii* X *Carex oshimensis*) X *Carex trifida* and hereinafter referred to by the name 'ET CRX 904'.

The new *Carex* plant is a product of a planned breeding program conducted by the Inventors in Boijl, The Netherlands. The objective of the breeding program was to create new compact *Carex* plants with an elegant plant habit.

The new *Carex* plant originated from a cross-pollination conducted by the Inventors in Boijl, The Netherlands in August, 2017 of a proprietary selection of *Carex morrowii* X *Carex oshimensis* identified as code number 13-77, as the female, or seed, parent, not patented, with a proprietary selection of *Carex trifida* identified as code number 210, as the male, or pollen, parent, not patented. The new *Carex* plant was discovered and selected by the Inventors as a single plant from within the progeny of the stated cross-pollination grown in a controlled greenhouse environment in Boijl, The Netherlands in July, 2018.

Asexual reproduction of the new *Carex* plant by in vitro meristem culture in a controlled greenhouse environment in Boijl, The Netherlands since August, 2018 has shown that the unique features of this new *Carex* plant are stable and reproduced true to type in successive generations.

SUMMARY OF THE INVENTION

Plants of the new *Carex* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ET CRX 904'. These characteristics in combination distinguish 'ET CRX 904' as a new and distinct *Carex* plant:

1. Relatively compact and broad outwardly arching plant habit.
2. Moderately vigorous to vigorous growth habit.
3. Long linear yellow green, light yellow and white variegated leaves.
4. Good garden performance.

Plants of the new *Carex* differ primarily from plants of the female parent selection in the following characteristics:

1. Leaves of plants of the new *Carex* are longer than leaves of plants of the female parent selection.
2. Leaves of plants of the new *Carex* are darker green in color than leaves of plants of the female parent selection.

Plants of the new *Carex* differ primarily from plants of the male parent selection in the following characteristics:

1. Plants of the new *Carex* are more compact than plants of the male parent selection.
2. Leaves of plants of the new *Carex* are shorter and narrower than leaves of plants of the male parent selection.

Plants of the new *Carex* can be compared to plants of the *Carex hybrida* 'ET CRX01', disclosed in U.S. Plant Pat. No. 26,199. In side-by-side comparisons, plants of the new *Carex* differ primarily from plants of 'ET CRX01' in the following characteristics:

1. Plants of the new *Carex* are more compact than plants of 'ET CRX01'.
2. Leaves of plants of the new *Carex* are shorter and narrower than leaves of plants of 'ET CRX01'.
3. Leaves of plants of the new *Carex* have yellow green-colored margins with light yellow to white-colored centers whereas leaves of plants of 'ET CRX01' have green-colored centers and white-colored margins.

BRIEF DESCRIPTION OF THE PHOTOGRAPHS

The accompanying photographs illustrate the overall appearance of the new *Carex* plant showing the colors as true as it is reasonably possible to obtain in colored reproductions of this type. Colors in the photographs may differ slightly from the color values cited in the detailed botanical description which accurately describe the colors of the new *Carex* plant.

The photograph on the first sheet (FIG. 1) is a side perspective view of a typical plant of 'ET CRX 904' grown in a container.

Figure 2:
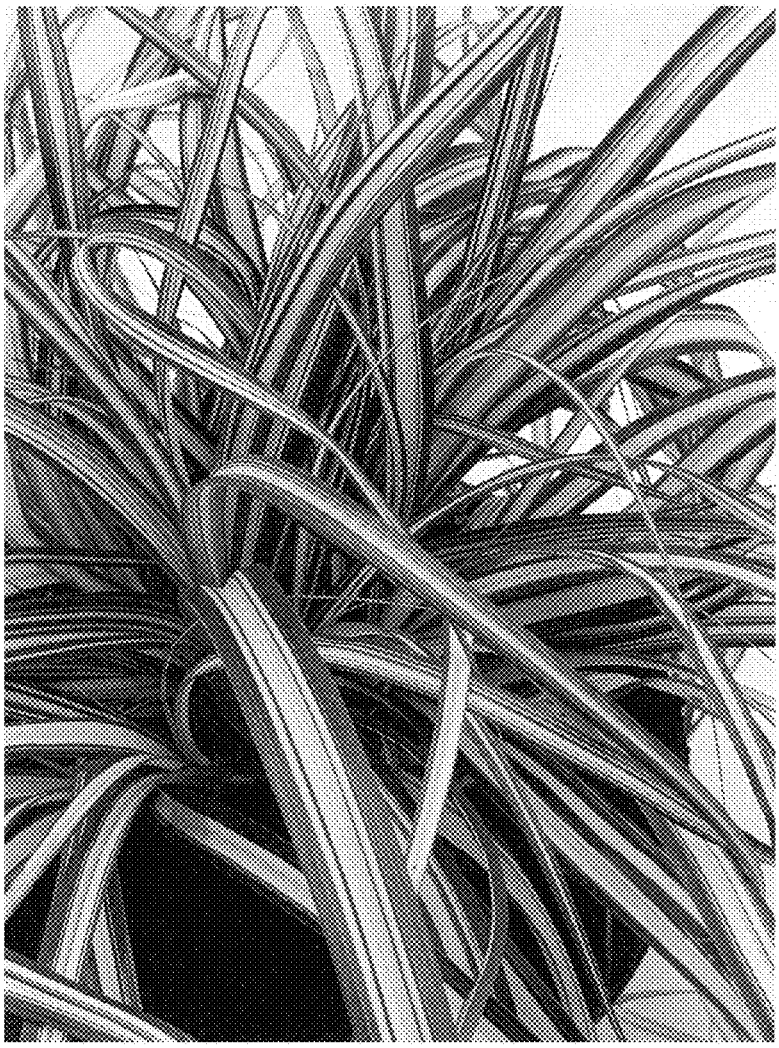

The photograph on the second sheet (FIG. 2) is a close-up view of a typical plant of 'ET CRX 904'.

Figure 3:
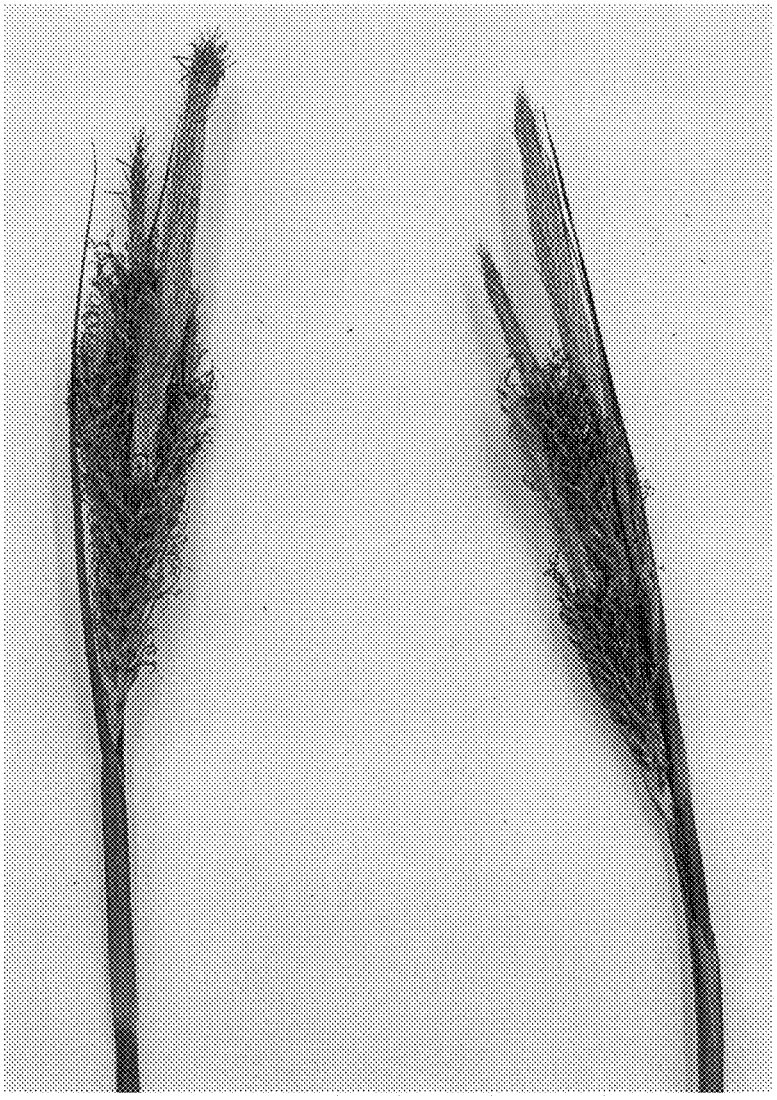

The photograph on the third sheet (FIG. 3) is a close-up view of typical inflorescences of 'ET CRX 904'.

DETAILED BOTANICAL DESCRIPTION

The aforementioned photographs and following observations and measurements describe plants grown during the spring in 26-cm containers in an outdoor nursery in Boijl, The Netherlands and under cultural practices typical of commercial *Carex* plant production. During the production of the plants, day temperatures ranged from 18° C. to 32° C. and night temperatures ranged from 6° C. to 20° C. Plants were one year old when the photographs and botanical description were taken. In the following description, color references are made to The Royal Horticultural Society Colour Chart, 2001 Edition, except where general terms of ordinary dictionary significance are used.

Botanical classification: (*Carex morrowii* X *Carex oshimensis*) X *Carex trifida* 'ET CRX 904'.

Parentage:

*Female, or seed, parent.*—Proprietary selection of *Carex morrowii* X *Carex oshimensis* identified as code number 13-77, not patented.

*Male, or pollen, parent.*—Proprietary selection of *Carex trifida* identified as code number 210, not patented.

Propagation:

*Type.*—By in vitro meristem culture.

*Time to initiate roots, summer.*—About six weeks at soil temperatures about 15° C. and ambient temperatures about 20° C. to 30° C.

*Time to produce a rooted young plant, summer.*—About three months at soil temperatures about 15 ° C. and ambient temperatures about 20° C. to 30° C.

*Root description.*—Medium in thickness, fleshy; color, close to 162D, actual color of the roots is dependent on substrate composition, water quality, fertilizer type and formulation, substrate temperature and physiological age of roots.

*Rooting habit.*—Freely branching habit; medium density.

Plant description:

*Plant and growth habit.*—Relatively compact and broad outwardly arching plant habit; about 30 main shoots (culms) develop from the base; moderately vigorous to vigorous growth habit; moderate to fast growth rate.

*Plant height, soil level to top of foliar plane.*—About 20 cm.

*Plant diameter or spread.*—About 35 cm to 40 cm.

Leaf description:

*Arrangement.*—Alternate; sessile; about 15 leaves per culm.

*Length.*—About 30 cm to 40 cm.

*Width.*—About 8 mm to 10 mm.

*Shape.*—Linear; strongly curved and arching.

*Apex.*—Long acuminate to long aristate.

*Margin.*—Appears to be entire, but actually very finely serrate and sharp to the touch.

*Base.*—Sheathing; length of leaf sheath, about 2.5 cm to 3 cm; close to 197B to 197C in color.

*Texture and luster, upper surface.*—Smooth, glabrous; glossy.

*Texture and luster, lower surface.*—Smooth, glabrous; moderately glossy.

*Venation pattern.*—Parallel.

*Color.*—Developing and fully expanded leaves, upper surface: Towards the margins, close to 143B and 144A; centers, proximally, close to 151D, mid-section, close to 160B and distally, close to 155C; venation, close to 139C. Developing and fully expanded leaves, lower surface: Towards the margins, close to 143A to 143B; centers, close to 160B; venation, close to 138A.

Flower description:

*Flower type and arrangement.*—Terminal racemes with staminate and pistillate flowers arranged on spikelets; inflorescences upright and held above and beyond the foliar plane on strong peduncles.

*Inflorescence height.*—About 5 cm to 8 cm.

*Inflorescence width.*—About 2 cm to 3 cm.

*Flowering habit.*—Freely flowering with about 50 inflorescences developing per plant with about three to four flowers per spikelet.

*Flowering time.*—Plants begin flowering about eight to nine months after planting; plants flower continuously from late winter until late spring in The Netherlands.

*Fragrance.*—None detected.

*Flower buds.*—Length, staminate and pistillate flowers: About 3 cm to 4 cm. Diameter, staminate and pistillate flowers: About 3 mm. Shape, staminate and pistillate flowers: Linear. Color, staminate flowers: Close to N199B to N199C. Color, pistillate flowers: Close to 144A and 145A.

*Spikelets.*—Diameter: About 1.5 cm. Depth: About 3 cm to 4 cm. Shape: Sedge-like, narrowly ovate. Persistence of spikelets: Persistent. Staminate flowers: Typically with one lemma and one glume. Lemma and glume: Length: About 5 mm to 6 mm. Width: About 0.5 mm. Shape: Lanceolate. Apex: Long and narrowly acute. Margin: Entire. Texture and luster, upper and lower surfaces: Smooth, glabrous; matte. Color, upper and lower surfaces: Close to 11C to 11D. Pistillate flowers: Typically with one lemma and no glume. Lemma: Length: About 5 mm. Width: About 1 mm. Shape: Lanceolate. Apex: Long and narrowly acute. Margin: Entire. Texture and luster, upper and lower surfaces: Smooth, glabrous; matte. Color, upper and lower surfaces: Close to 145D; towards the apex, close to 11C to 11D.

*Peduncles.*—Length: About 18 cm to 20 cm. Diameter: About 3 mm to 5 mm. Aspect: About 20° from vertical. Strength: Strong. Texture and luster: Smooth, glabrous; matte. Color: Distally, close to 137B and proximally, close to 151B to 151C.

*Reproductive organs.*—Stamens: Quantity per flower: Numerous. Anther length: About 4 mm to 5 mm. Anther shape: Oval. Anther color: Close to 11D. Pollen amount: Abundant. Pollen color: Close to 11C. Pistils: Quantity per flower: One. Pistil length: About 1 mm to 2 mm. Style length: About 1 mm. Style color: Close to 145A to 145B. Stigma shape: Fimbriate. Stigma color: Close to N199B to N199C. Ovary color: Close to 145A.

*Fruits and seeds.*—To date, fruit and seed production has not been observed on plants of the new *Carex*.

Pathogen & pest resistance: To date, plants of the new *Carex* have not been shown to be resistant to pathogens and pests common to *Carex* plants.

Garden performance: Plants of the new *Carex* have been observed to have good garden performance and to tolerate wind, rain and temperatures ranging from about −20° C. to about 35° C.

It is claimed:

1. A new and distinct *Carex* plant named 'ET CRX 904' as illustrated and described.

* * * * *